United States Patent [19]

Konigsberg et al.

[11] Patent Number: 5,258,499
[45] Date of Patent: Nov. 2, 1993

[54] LIPOSOME TARGETING USING RECEPTOR SPECIFIC LIGANDS

[75] Inventors: Paula J. Konigsberg, Pasadena; Leroy L. Richer, San Gabriel; Paul G. Schmidt, San Marino; Joseph A. Uliana, Sierra Madres, all of Calif.

[73] Assignee: Vestar, Inc., San Dimas, Calif.

[21] Appl. No.: 850,019

[22] Filed: Mar. 10, 1992

Related U.S. Application Data

[63] Continuation-in-part of Ser. No. 713,549, Jun. 7, 1991, abandoned, which is a continuation of Ser. No. 353,250, May 16, 1989, abandoned, which is a continuation-in-part of Ser. No. 194,636, May 16, 1988, abandoned.

[51] Int. Cl.[5] .................. A61K 37/02; C07K 3/08; C07K 15/08
[52] U.S. Cl. .................. 530/351; 424/85.1; 424/85.2; 424/450; 530/402; 530/408; 530/409; 530/410
[58] Field of Search .................. 424/85.1, 85.2, 450; 530/402, 351, 408, 409, 410

[56] References Cited

U.S. PATENT DOCUMENTS

| | | | |
|---|---|---|---|
| 4,480,041 | 10/1984 | Myles et al. | 435/7 |
| 4,598,051 | 7/1986 | Papahadjopoulos et al. | 436/512 |
| 4,671,958 | 6/1987 | Rodwell et al. | 530/389.6 |
| 4,762,915 | 8/1988 | Kung et al. | 530/405 |
| 4,806,466 | 2/1989 | Papahadjopoulos et al. | 435/7 |

FOREIGN PATENT DOCUMENTS

| | | |
|---|---|---|
| 0274219 | 7/1988 | European Pat. Off. |
| 2564319 | 5/1984 | France |
| 8604232 | 7/1986 | PCT Int'l Appl. |
| 8707150 | 12/1987 | PCT Int'l Appl. |
| 2157172 | 10/1985 | United Kingdom |

OTHER PUBLICATIONS

Garcon et al., Biochem. Soc. Trans., vol. 14 (6) pp. 1038–1039 (1986).
Salord et al., Biochem. Biophys. Acta. vol. 886(1) pp. 64–75 (1986).
Bakouche et al., Lymphokine Res. vol. 7(4) pp. 445–456 (1988).
Derksen et al. Biochim. Biophys. Acta 814, 151–155 (1985).
Martin et al. J. Biol. Chem. 257, 286–288 (1982).
Pemawansa et al., "An Advanced Affinity Membrane for Covalent Binding of Amino Ligands", BioTechniques, 9 (1990) 352–356.
"Liposomes Expressing IL 1 Biological Activity" O. Bakouche et al. J. of Immunology 138 (1987) 4256–4262.
"Targeted Liposomes: A Method for Preparation and Analysis" V. Jansons et al., Anal. Biochem. 111 (1981) 54–59.
"Protein Immobilization on the Surface of Liposomes via Carbodiimide Activation in the Presence of N-hydroxyfulfosuccinimide" A. Bogdanov et al. Febs Letters 231 (1988) 381–384.
"Enhancement of the Protective Efficacy of Inactivated Influenza A Virus Vaccine in Aged Mice by IL-2 Liposomes" I. Mbawuike et al., Vaccine 8 (1990) 347–352.
"Enhancement of Interleukin-2 Activity by Liposomes" M. L. Joffret et al. Vaccine 8 (1990) 385–389.
Form PCT/ISA/220 mailed Sep. 5, 1989 for Application PCT/EP 89/00521.

Primary Examiner—Jeffrey E. Russel
Assistant Examiner—Eric Linnell
Attorney, Agent, or Firm—Adam Cochran; George A. Gilbert

[57] ABSTRACT

Delivery vehicle formulations comprise active agents encapsulated within liposomal vesicles to which are attached protein hormones (ligands) such as interleukin-2. The ligands are capable of showing affinity for specific cell receptors resulting in delivery of the encapsulated active agent to target cells, enabling delivery of active agents to particular cell populations in the treatment of conditions such as immune system disorders.

4 Claims, 7 Drawing Sheets

- ● 125 I-IL-2
- ○ COLD IL-2-20μℓ (25μg/ml)
- × SMPB-IL-2-100μℓ (1.8μg BCA)
- □ DEACETYLATED SUV+SMPB IL-2-100μℓ
- △ NON DEACETYLATED SUV+SMPB IL-2-100μℓ

LIPOSOME TARGETING USING RECEPTOR SPECIFIC LIGANDS

This is a continuation of co-pending application Ser. No. 07/713,549 filed on Jun. 7, 1991, now abandoned, which is a continuation of co-pending application Ser. No. 07/353,250, filed on May 16, 1989, now abandoned, which is a continuation-in-part of application Ser. No. 07/194,636, filed May 16, 1988, now abandoned.

FIELD OF THE INVENTION

This invention relates generally to the field of biochemistry, and more particularly to delivery vehicle formulations comprising one or more therapeutic or diagnostic agents encapsulated within liposomes to which are bound ligands specific for particular cell receptors. Also provided are methods for the preparation of such formulations.

BACKGROUND OF THE INVENTION

Animal cells have receptors on the outer surface which bind molecules having specific receptor binding domains, resulting in an effect on the biological function of the cells. If this function is incompatible with the well being of the host, these receptor specific molecules could be employed to deliver therapeutic agents to the cell if the agents could be attached to such molecules without destroying the ability of the molecule to bind to the cell surface.

Abnormal, and in some situations even normal functioning of particular cell types may precipitate life threatening or other disease conditions. In immune system dysfunction, the inappropriate activity of T lymphocytes (T cells) plays a particularly prominent part, and therapy now frequently consists of treatment with strong immunosuppressive agents. However, many of these treatments result in widespread toxicity and resulting damage to the immune system frequently extends beyond the particular cell type causing the disorder. Thus, the recovering patient may be left temporarily stripped of defenses against infectious pathogens. A better therapy for conditions such as autoimmune disease and graft rejection would be one that concentrates only on those clones of T cells that are activated by inappropriate targets, leaving intact the remaining T lymphocytes and other cells of the immune system.

An important feature that distinguishes activated from resting T cells is the expression of high affinity receptors for interleukin-2 (IL-2). There are two IL-2 receptors, high- and low affinity. The low affinity receptor is found on both resting and activated T cells, while the high affinity receptor is found only on activated cells and is the receptor involved in the internalization of interleukin-2.

After contact with cellular antigens that they recognize, certain T cells secrete lymphokines, including interleukin-2, that mediate a variety of immune functions. In addition, all T cells respond to antigen activation by expressing receptors for interleukin-2, thereby becoming responsive to the powerful growth-promoting effects of this hormone. The resulting proliferation amplifies the number of cells available to react to the current antigenic challenge. When the antigen is cleared, the number of high affinity interleukin-2 receptors is reduced.

Targeting of particular cell classes, including cells of the immune system, has been attempted. In particular, monoclonal antibodies (MoAbs) against the human low affinity interleukin-2 receptor are available, and some groups have explored the use of such monoclonal antibodies coupled to cytotoxic agents to target interleukin-2 receptor-bearing leukemic T cells for destruction.

Liposomes with antibodies attached to their surfaces have been shown to bind specifically to cells expressing a cell surface antigen. A problem in delivering cytotoxic agents as conjugates with antibodies against the interleukin-2 receptor is that the antibody is not internalized. The high affinity interleukin-2 site is primarily associated with the internalization of interleukin-2. As one result of the low frequency of internalization of antibodies, impractically high concentrations of antibody-toxin conjugate must be used, with a corresponding increased risk of toxicity to bystander (non-interleukin-2 receptor bearing) cells.

While it is known to covalently link certain antibodies to liposomes subsequent to the random partial protection of $-NH_2$ functional groups of the antibody (Jansons, et al., 1981 *Anal. Biochem.* 111, 54), attempts to couple receptor specific proteins to therapeutic agents or liposomes in order to achieve targeted delivery to particular cell populations have not been successful due to the fact that the existing coupling processes have failed to provide a means to ensure that the receptor binding domain on such a protein is not destroyed, and thus remains accessible for later interaction with cell receptor sites.

Although chemical techniques are available for linking proteins to liposomes, these techniques are nonselective in nature and involve linkages which will block or otherwise interfere with the receptor binding domain on the protein. Thus, it has been a desideratum to provide a liposome having a protein hormone with active receptor binding domains attached thereto, and means for binding protein hormones such as interleukin-2 to hposomes while protecting the receptor binding domain of the protein.

SUMMARY OF THE INVENTION

The invention includes a composition of matter comprising a liposome which is covalently bound to a ligand, in particular a cytokine, having an unblocked receptor binding domain for cell surface receptor site interaction, the domain being accessible for such interaction.

The process for preparing a liposome/ligand complex comprises coupling a liposome to a ligand having a receptor binding domain capable of interacting with a cell receptor site, with the receptor binding domain on the ligand having been selectively protected prior to the coupling. The process may comprise fixing a coupling agent to a liposome which is then joined to a ligand; fixing a coupling agent to a ligand which is then joined to a liposome; or preferably fixing a first coupling agent to a liposome and a second coupling agent to the ligand, and then joining the respective coupling agents to form the liposome/ligand conjugate. During these processes, the receptor binding domain on the ligand is protected whenever it would preferentially react with the coupling agent.

The term ligand, as used herein, is defined as being a protein hormone, i.e., a protein moiety having a receptor binding domain and which is capable of eliciting a metabolic response in a target cell. More preferably the ligand is a cytokine (either natural or synthetic as used herein without specific qualifying language), that is, a protein hormone which controls the immune system through receptor specific activity. Most preferably, the cytokine is interleukin-2. It should be understood that this definition of the term ligand excludes antibodies. The receptor binding domain on a protein hormone is that region which uniquely interacts with the cell-surface receptor for that protein hormone. For interleukin-2, the receptor binding domain has been determined to be that region of the molecule comprising amino acid residues 20 to 30.

A wide variety of liposomes may be used in the invention (including oligo- or multilamellar vesicles); but preferably the liposomes are small unilamellar vesicles (SUVs) having an external diameter of from about 30 to about 300 nanometers (nm), most preferably 50 to 100 mn. The liposomes are preferably composed of various ratios of distearoyl phosphatidylcholine, phosphatidylethanolamine and/or cholesterol as well as other lipids, and include a biologically active agent, which is referred to herein as an active agent and used to mean a compound having a therapeutic or diagnostic effect. As those skilled in the art will appreciate, the liposome/ligand formulations of the present invention are amenable to encapsulation of a wide variety of agents while still retaining the receptor site specificity of the desired attached ligand. In a preferred embodiment, the liposomes encapsulate one or more immunosuppressive or cytotoxic agents. In particular, the encapsulated active agents may be a cyclosporin or methotrexate.

Multilamellar vesicles may be obtained by simple agitation of an aqueous mixture of pholpholipids, and sonification of these structures leads to the formation of SUVs. Standard methods for the formation of liposomes are reported in Szoka et al., *Ann. N.Y. Acad. Sci* 308, 1–482 (1978) and Paznanstey et al, *Pharmacological Review* 36, 277–336 (1984), the disclosures of which are incorporated herein by reference.

The formulations include liposomes to which are attached one or more ligands, where the ligands retain their binding specificity, or affinity, for specific receptors which exist on the surface of target cells. Preferential in vivo delivery, or targeting, of the delivery vehicle to the desired target cell population, and release or internalization of the active agent at the receptor cell site, is achieved by virtue of the preserved affinity of the liposome attached ligand, for the particular target cell receptor. By this method, the function or other characteristics of the target cell population may be directly affected by action of the delivered therapeutic agent. Advantages of extended circulatory and serum stability and reduced effective dosages ensue.

A preferred embodiment of the delivery vehicle formulation comprises small unilamellar phospholipid vesicles encapsulating one or more active agents, covalently attached to the ligand interleukin-2 and capable of interacting with internalizing high affinity receptor sites of activated T or B cells, or to cells of the monocytic-macrophage series. Significant advantages are provided in that coupling of a drug bearing liposome to interleukin-2 in this manner permits both the internalization of the drug and the specific targeting of activated T cells, as opposed to the prior art which targets low affinity receptors with antibody/drug conjugates. In addition, liposomes deliver a much larger payload of an active agent to targeted cells. In this preferred embodiment, the interleukin-2 ligand may comprise only that portion of the interleukin-2 molecule that possesses the site for binding to internalizing cell receptors.

The ligands are covalently attached to the liposome surface by coupling agents (linker molecules) which are covalently bonded to the ligand while the receptor binding domain on the ligand is protected. Preferably, the ligand is attached to the liposome by forming a liposome bound to a first coupling agent, a ligand having an unblocked receptor domain bound to a second coupling agent, and then joining liposome and ligand coupling agents to anchor the ligand to the liposome, leaving the receptor binding domain of the ligand physically available for interaction in vivo. The receptor domain may be protected by transient antibody binding prior to coupling, or may be temporarily protected by chemical agents during the initial coupling step. In addition, steric hindrance between the liposome and the ligand is avoided through the use of a 4 to 6 carbon linker arm. Lysine residues on the ligand are preferred for coupling. Alternatively, the ligand interleukin-2 may be attached to the liposome by non-lysine residues, e.g., by cysteine, histidine or arginine residues, to avoid disturbance of the lysine residues which are located in the cell receptor binding site.

In a preferred embodiment, two coupling agents are employed. The first coupling agent (for bonding to the liposome) is a beterobifunctional agent, preferably a sulfo-n-hydroxy suceinimidyl compound such as succinimidyl-S-acetylthioacetate (SATA) or N-hydroxy succinimidyl-3-(2-pyridyldithio)-proptionate (SPDP); and most preferably SATA.

The second coupling agent (for bonding to the ligand) is a heterobifunctional agent, preferably a member of the group consisting of succinimidyl-4-(p-maleimidophenyl) butyrate (SMPB), sulfo-SMPB, N-(4-carboxy-cyclohexylmethyl) maleimide (SMCC), sulfo-SMCC, m-maleimidobenzoyl-N-hydroxysuccinimide ester (MBS), sulfo-MBS, N-succinimidyl (4-iodoacetyl) aminobenzoate (SIAB) and sulfo-SIAB; and most preferably SMPB.

In one embodiment, the novel compound succinimidyl-S-acetylthioacetatephosphatidylethanolamine (SATA-PE) is used to produce activated novel phospholipid vesicles including SATA in the outer bilayer which will covalently bond with a maleimide bearing ligand conjugate such as the SMPB/interleukin-2 conjugate of the invention.

BRIEF DESCRIPTION OF THE DRAWINGS

FIG. 1 is a diagrammatic representation of the interleukin-2 molecule;

FIG. 2 depicts a reaction for protection of the receptor binding domain of interleukin-2, in which PA indicates Protein A agarose, aIL-2 indicates the IL-2 antibody, and PA/IL-2 is IL-2 bound to the antibody resin;

FIG. 3 depicts a reaction for modifying the PA/IL-2 with SMPB;

FIG. 4 is a graphical representation of the behavior of modified interleukin-2 in the receptor binding assay;

FIG. 5 depicts a protocol for the modification of phosphatidylethanolamine (PE) with SATA;

FIG. 6 depicts a protocol for generating a covalent bond between interleukin-2 and liposomes with SMPB/interleukin-2 to form a conjugated IL-2;

FIG. 7 is a graphical representation of the interleukin-2 receptor binding assay using SUV liposome/IL-2 delivery vehicles;

FIG. 8 depicts a preferred reaction for preparation of activated lipids as described in Example 2;

DETAILED DESCRIPTION

The present invention relates to the production of various delivery vehicle formulations and to methods for attaching biorecognition molecules (ligands) to the surface of liposomes in ways which, in a preferred embodiment, covalently bind the ligands to the liposomes while retaining the receptor binding domains of the molecules intact and functional. A preferred biorecognition molecule for use as a ligand is the cytokine interleukin-2. The present invention is directed in part to surmounting several of the drug delivery problems previously encountered. Such problems include lack of targeting or cell specificity of the therapeutic agents, as well as cytotoxicity due to the high concentrations required in part to overcome such non-specificity.

Phospholipids are amphipathic molecules which are the primary constituents of cell membranes. Typical phospholipid hydrophilic groups include phosphatidylcholine and phosphatidylethanolamine moieties, while typical hydrophobic groups include a variety of saturated and unsaturated fatty acid moieties. Mixture of a phospholipid in water causes spontaneous organization of the phospholipid molecules into a variety of characteristic phases depending on the conditions used. These include bilayer structures in which the hydrophilic groups of the phospholipids interact at the exterior of the bilayer with water, while the hydrophobic groups interact with similar groups on adjacent molecules in the interior of the bilayer. Such bilayer structures can be quite stable and form the principal basis for cell membranes.

Phospholipid bilayer structures can also be formed into closed spherical shell-like structures which are called phospholipid vesicles or liposomes. The membrane bilayers in these structures typically encapsulate an aqueous volume, and form a permeability barrier between the encapsulated volume and the exterior solution. SUVs consist of a single closed bilayer shell, and typically are on the order of 50 to 100 nanometers (nm) (5 to $10 \times 10^{-8}$ meters) in exterior diameter. Such SUVs may have sizes outside of these range, as for example from about 30 to about 300 nm. However, the range of 50 to 100 nm is considered to be optimal from the standpoint of, e.g., maximal circulation time in vivo.

More particularly, phospholipids dispersed in aqueous solution spontaneously form bilayers with the hydrocarbon tails directed inward and the polar headgroups outward to interact with water. Simple agitation of the mixture usually produces multilamellar vesicles (NMVs), structures with many bilayers in an onion-like form having diameters of 1-10 μm (1000-10,000 mn). Sonication of these structures leads to formation of SUVs having an average diameter of about 30-300 nm. The actual equilibrium diameter is largely determined by the nature of the phospholipid used and the extent of incorporation of other lipids such as cholesterol.

Either as MLVs or SUVs, liposomes have proven valuable as vehicles for drug delivery in animals and in humans. Active drugs, including small hydrophilic molecules and polypeptides, can be trapped in the aqueous core of the liposome, while hydrophobic substances can be dissolved in the liposome membrane. The liposome structure can be readily injected and form the basis for both sustained release and drug delivery to specific cell types, or parts of the body. MLVs, primarily because they are relatively large, are usually rapidly taken up by the reticuloendothelial system (the liver and spleen) which is referred to as the RES. On the other hand, SUVs, if properly formulated, may have circulation times of many hours.

The invention typically utilizes vesicles which remain in the circulatory system for at least hours, demonstrate specificity for a select cell population and ultimately break down in proximity to the target cell or after internalization by the target cell. For these requirements the formulations preferably utilize SUVs. Preferred liposome compositions include various mole ratios of distearoyl-phosphatidylcholine (DSPC) and cholesterol and dipalmitoylphosphatidyl-choline (DPPC) and cholesterol, and most preferably include SATA/PE, or PE for linking with SATA, as described.

The vesicle delivery vehicles described herein are preferably liposomal structures capable of incorporation, as by encapsulation, of an active agent useful for the treatment or diagnosis of a mammalian disease or physiological condition, in a manner suitable for administration to the mammalian body. Small unilamellar liposomes are preferred, although MLVs or other liposomes such as micelles or polymeric microspheres or matrices may also be employed. A distinguishing characteristic of such liposomes is their ability to be bound to an appropriate ligand in a manner which preserves the ability of the ligand to associate with specific cellular receptor sites while enhancing delivery and/or incorporation of the liposome and its incorporated active agent to the desired cell population.

The liposome/ligand system also allows the possibility of multiple binding interactions to the target cell. This, of course, depends on the number of ligands per vesicle and mobility of the ligands and receptors in their respective membranes. However, since the effective binding constant increases as the product of the binding constants for each site, there is a very substantial advantage to multiple binding interactions.

Figure 1:
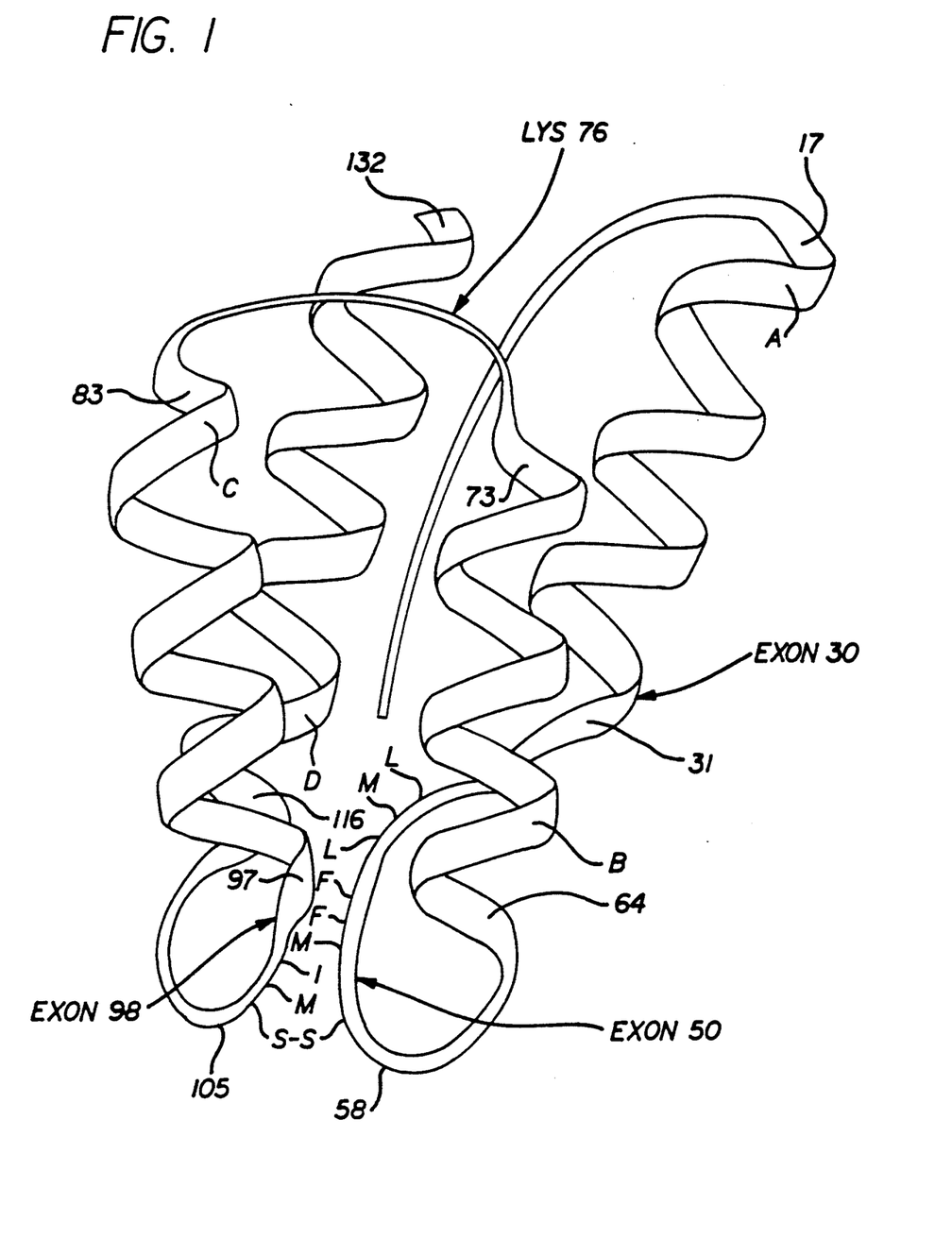

A preferred ligand is interleukin-2 (see FIG. 1). This cytokine is particularly suitable to effect targeting of the present delivery vehicles to specific activated T and B cell populations in view of its particular specificity for the high affinity interleukin-2 receptors on such cells.

Interleukin-2 acts in vivo as a paracrine hormone, with a short term half-life. For in vivo use, it may be desirable to use a form of recombinant interleukin-2 as starting material that has already been stabilized by certain amino acid substitutions, e.g., is replacing the nonpaired Cys-125 with Ser or Ala. In addition, abbreviated forms of the interleukin-2 molecule, as for example portions containing the cellular receptor binding domain in the region of amino acid residues 20 to 30 of the molecule, may also provide useful ligands capable of interacting specifically with cellular receptors while attached to liposomes according to present invention.

Among the other cytokine ligands which are within the scope of the invention, are the following cytokines: antigrowth factors; B cell growth factors including BPA (burst promoting activity); chalones; chemotactic factors; colony stimulating factors such as GM-CSF and G-CSF; growth factors; interferon $\alpha$; interferon $\beta$; interferon gamma; interleukin-1 $\alpha$; interleukin-1 $\beta$; interleukins 1 to 7; lymphotoxin; tumor necrosis factor;

macrophage inhibitory factor and T cell replacing factor.

The ligands which may be most simply bound to a liposome are those which are already adapted to be incorporated into or associated with a membrane. Glycolipids, glycoproteins, lipoproteins, or hydrophobic proteins are examples of molecules which can be bound or associated with appropriate liposomes as part of the lipid mixture.

An important feature of the invention involves production of a useful liposome-protein complex by the choice of chemical cross linking techniques. The most appropriate system for use in the present invention includes heterobifunctional reagents to modify and thereby provide means to activate for chemical reaction the free amino group of PE, which is then incorporated into liposomes sequestering a drug or marker of interest.

Superior results have been obtained by using a preferred method which employs SATA to modify the amino group of the lipid (PE) to form SATA-PE which is incorporated into the outer bilayer of the liposome, and SMPB to modify the lysine $\epsilon$-amino groups of the protein ligand so as to provide reactive groups capable of binding the ligand to the liposome. Facile reaction then occurs between the activated (modified) phospholipid vesicle and protein reactive group to create the liposome/IL-2 conjugate.

Since interleukin-2 binds with high specificity to receptors on activated T cells, the present invention in a preferred embodiment uses interleukin-2 linked to the surface of phospholipid vesicles. Such modified liposomes then bind preferentially to T cells expressing the high affinity interleukin-2 receptor. This approach provides a mechanism for delivering active molecules such as active agents to the vicinity of those T cells expressing the high affinity interleukin-2 receptor, under normal conditions. As noted above, using interleukin-2 as a ligand or determinant provides a mechanism for extremely selective targeting of cytotoxic reagents to the subclass of T cells expressing this receptor, as well as to B cells or other cells that express it.

An advantageous method for attachment of interleukin-2 is to link the interleukin-2 protein molecule to the surface of a preformed liposome. This insures that the entirety of the molecule is on the outside surface, free from interaction with any encapsulated materials and available for interaction with interleukin-2 receptors.

Prior to binding of a ligand such as interleukin-2 to an appropriate liposome or chemically modifying it preparatory to such binding, it may be extremely important to protect the receptor binding domain on the molecule from undesirable reactions or modifications. Thus, the coupling schemes presently available are generally non-selective in nature and will typically yield products in which the receptor binding domain of the ligand is substantially blocked or otherwise interfered with after linkage to the liposome. The present invention surmounts this problem by providing means to reversibly protect, prior to activation and/or linkage of the ligand, the portion of the ligand responsible for interaction with the cellular receptor site. After linkage of the ligand to the liposome, or in any event after performing any reaction steps that might otherwise result in interference with or blocking of the receptor binding domain, the protected receptor binding domain of the ligand is freed of its protection means to yield a site capable of interacting with the appropriate cellular receptors.

Figure 2:
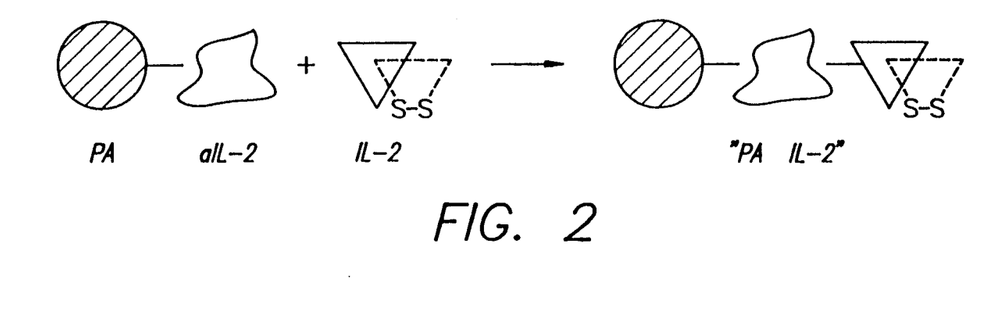

In the case of interleukin-2, it has been discovered that such protection can be accomplished using a murine monoclonal antibody directed to the region of the receptor binding domain at residues 20-30 (the shaded portions of the molecule in FIG. 1). According to such a procedure, such a MoAb is coupled to a stationary phase, e.g., a resin or gel such as Protein A Agarose, and interleukin-2 is then bound to the resin-linked antibody. It is then possible to modify one or more $\epsilon$-amino groups of the available lysine residues while the interleukin-2 is protected. A commercially available ELISA (Genzyme Corp.) using the murine monoclonal antibody directed to the region of the receptor binding domain at residues 20-30 (commercially available from Genzyme as catalog #DMS-1) showed that modified interleukin-2 would be recognized by this MoAb and that the MoAb would indeed be suitable as a blocking group. The protocol for use of such a resin is shown in FIG. 2, in which aIL-2 indicates the resin-linked antibody.

Data obtained from these experiments indicate that by blocking the receptor binding domain with the MoAb it is possible to obtain chemically modified interleukin-2 that retains its biological activity. Moreover, the antibody resin is reusable.

More particularly, investigations relating to the present invention have shown that linker-modified interleukin-2, that has been protected prior to linker addition according to the present invention, has a substantially increased capacity to compete with native interleukin-2 for receptor sites on lymphocytes as compared to linker-modified interleukin-2 that has not been so protected. Thus, interleukin-2 coupled with SMPB after protection as described herein is approximately two-and-one-half times more effective in competing with $^{125}$I-labeled interleukin-2 for murine HT2 T cell receptor sites than interleukin-2 coupled with SMPB without such protection.

EXAMPLE 1

Protection and Modification of the Ligand IL-2

Protein A Agarose (PA) resin for interleukin-2 is made as follows. Purified MoAb ($\alpha$-interleukin-2: Genzyme catalog #DMS-1) is combined with Protein A-Agarose in PBS for 60 minutes at 4° C. Protein G may also be used in a similar manner, and either Protein A or G may also be coupled to silica gel and used as described in this example. The resin is then washed in PBS, and the Protein A and $\alpha$-interleukin-2 crosslinked with 12.5% glutaraldehyde in PBS. The resin is again washed, and the amount of MoAb bound is determined by Lowry analysis of the supernatants as compared to the original concentration of MoAb.

Figure 3:
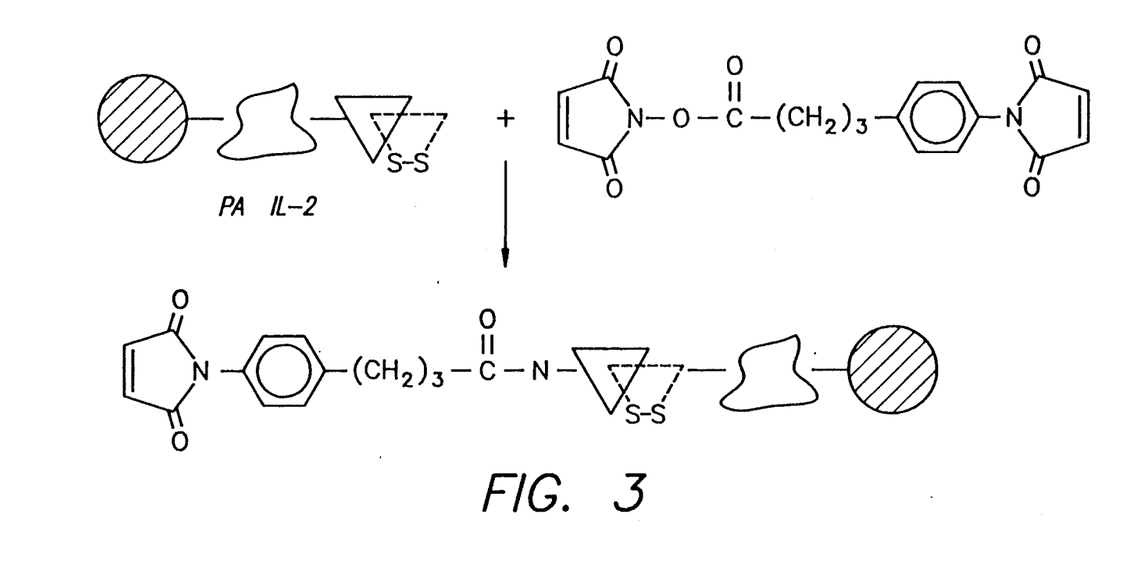
Figure 4:
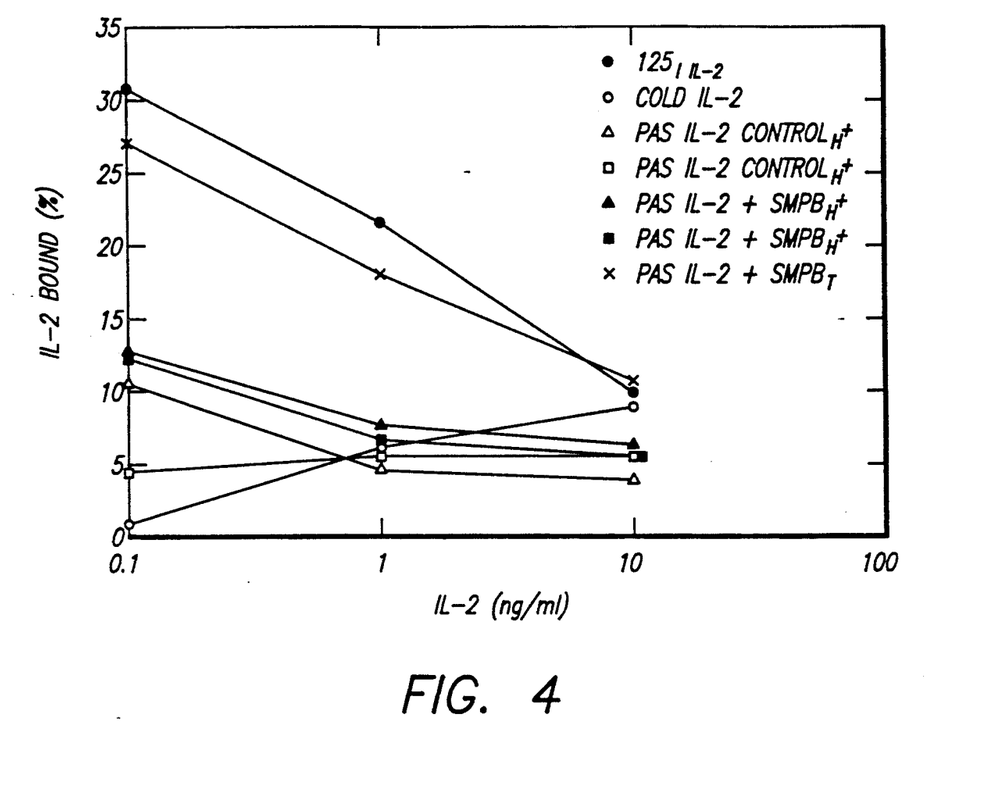

The high binding capacity of the Protein A-Agarose is sufficient to work in a volume of 100 $\mu$l while binding 25-50 $\mu$g of interleukin-2. Interleukin-2 is bound to the resin and modified with SMPB as indicated in FIG. 3. The modified interleukin-2 is then eluted from the resin with a first solution (0.2N acetic acid, pH 3.5), preferably followed by a second solution (1M Tris, pH 8.0). FIG. 4 shows the material eluted with the 0.2N acetic acid (H+), and the material eluted with the subsequent wash with 1M Tris (T), assayed by an interleukin-2 receptor binding assay using the CTLL2 cell line. The symbol PAS refers to material which has been eluted from the resin. Most preferably, the modified IL-2 is eluted with a first solution comprising a first chaotropic agent (2M NASCN) in 0.05M Tris (pH 8.0), preferably followed by a low pH solution of a second chaotrope (6% betaine in 0.2N acetic acid), all at 4° C. For the initial use of the resin, the contribution of the amino groups from both Protein A and the antibody is taken into account. Initially, a sample of Protein A silica gel resin with umnodified interleukin-2 is used as a control, but this is later discontinued if no adverse effects to the interleukin-2 are observed during the procedure.

The filled triangles and squares in FIG. 4 show the results of SMPB-IL-2 prepared on two different occasions. In these assays, no attempt is made to correct for concentration differences among samples yet the data indicate that SMPB-IL-2 is able to bind to the interleukin-2 receptor of these cells and to support growth.

The same effect of acid is observed when unmodified interleukin-2 is bound to the resin, eluted with acetic acid, and analyzed by the ELISA assay. In this assay, both the unmodified interleukin-2 and SMPB modified interleukin-2 were recognized by the monoclonal antibody to the receptor binding domain of interleukin-2.

In an alternate procedure, MBS (maleimidobenzoyl-N-hydroxy succinimide ester, a derivative of SMPB) is also used to modify interleukin-2. Use of this reagent also yielded biologically active interleukin-2 when assayed in a receptor binding assay and in the anti-IL-2 ELISA.

Synthesis of SATA-PE

SATA-PE is synthesized by a reaction which generates a modified PE having an acetyl thioester group on the ethanolamine moiety. For example, a five-fold molar excess of SATA is added to distearoyl phosphatidylethanolamine (DSPE) in a round bottom flask. Typically, 125 mg SATA is added to 75 mg of DSPE. 15 ml of $CHCl_3$:MeOH (1:1) is then added, followed by 100-135 $\mu$l of triethylamine. The flask is then flushed with nitrogen, sealed, and the reaction carried on for two hours at room temperature with stirring. The progress of the reaction is monitored by thin layer chromatography in $CHCl_3$:MeOH (7:3). The absence of a Ninhydrin positive, and the presence of a PMA positive spot having an Rf of 0.57 indicates the presence of SATA-PE. Some of this compound may oxidize to the disulfide (SATA-PE-SATA-PE), which has an Rf of about 0.37. It should be noted that SATA is quite labile and cannot be stored for prolonged periods. Accordingly, fresh reagent is preferably purchased prior to each procedure.

The material obtained is then evaporated to dryness and resuspended in 1.0 ml of $CHCl_3$:MeOH (1:1), and 15 ml of acetonitrile is added to the dry material. This solution is held at −20° C. for about 60 minutes to precipitate SATA-PE. Any unmodified DSPE remains in solution and precipitates at a much slower rate at this temperature. The precipitate is collected by filtration on a sintered glass filter and washed with acetonitrile. The washed SATA-PE is then again dissolved by the addition of 1:1 $CHCl_3$:MeOH and collected in a second filter flask, transferred to a preweighed flask and evaporated. The yield at this point has been between 80 and 84%.

During preparation, all steps should be conducted as quickly as possible to minimize oxidation. However, the removal of oxidized SATA-PE is accomplished by preparative thin layer chromatography, such as on a Kieselgel 60 plate obtained from EM Science. Aluminum backed silica gel (no fluorescent indicator) plates are used with $CHCl_3$:MeOH (7:3) as the mobile phase. SATA-PE is located by $I_2$ staining a strip cut from the end of the plate. The area containing SATA-PE is then cut out. The strips of $SiO_3$-coated aluminum are further cut up and extracted over a 30 minute period in 1:1 $CHCl_3$:MeOH. The SATA-PE is concentrated to dryness, dissolved in 1:1 $CHCl_3$:MeOH and dispensed into vials. Each vial is flushed with nitrogen and stored at −20° C.

Preparation of Liposomes

Liposomes having the composition DSPC:Cholesterol:SATA-PE(molar ratio 1.5:1.0:0.5) are prepared by dissolving the lipids (10 mgs total) in 1 ml of $CHCl_3$, drying to a film under nitrogen, then further drying under vacuum overnight. The lipid film is then dispersed in PBS (pH 8.3) at 65° C. for 20 minutes, sonicated with a probe sonicator for 6 minutes at 65° C., and annealed for 5 minutes at the same temperature to form SUVs. The liposomes are then centrifuged at 13,000×g for 10' to remove any particles of titanium from the sonicator probe.

The SUVs are then passed over a Sephacryl S300 column for removal of nonvesicle phospholipids. The column is preferably presaturated with 1% non-SATA-PE DSPC:Cholesterol (2:1) SUVs in PBS (pH 7.0), 1 mM EDTA, and 0.2 mM PMSF to maximize pass through of the SATA-PE liposomes. 0.9 ml of liposomes ($\approx$ 10 mg lipid) are loaded and vesicles are recovered in a volume of 2.4 ml. Approximately 3.3 mgs/ml of lipid were recovered. Liposomes produced in this manner have a mean diameter of about 50 nm. This method may be conducted with active agents in either the lipid film or the aqueous buffer, as appropriate. For example, the process of this example may be conducted wherein the PBS buffer contains 55 mg/ml methotrexate to form SUVs which encapsulate methotrexate.

Attachment of Modified IL-2 to Liposomes

The modified interleukin-2, shown to be biologically active, is covalently coupled through its maleimido groups to the preformed SUVs containing SATA-PE. The modification enables the SMPB-modified interleukin-2 to be covalently coupled to the free sulfhydryl exposed on the surface of the liposome. This novel reaction scheme, shown in FIG. 6, allows the preparation of liposomes containing a modified lipid which is chemically unreactive until needed. The modified lipid may thereafter be activated, as here for example, by deacetylating (deblocking) the SATA-PE compound using hydroxylamine, for reaction with a reactive group on the ligand, here SMPB modified interleukin-2. The liposome/IL-2 delivery vehicle prepared in this manner is able to compete effectively in the interleukin-2 receptor binding assay, as shown in FIG. 7. This method may be suitable for use with other recognition proteins as well.

Specifically, 10 $\mu$l of freshly prepared 0.5M hydroxylamine was added to 1 ml of the SATA-PE/SUVs prepared as described above (10 mg/ml in PBS), and the solution incubated for 30 minutes at 22° C. under argon. The pH of the SMPB-IL-2 prepared above was adjusted ot pH 6.5-7, and the SMPB-IL-2 was added to the deacylated SUVs in an amount of 10-20 pg for 12-24 mg lipid, and incubated for 2 hrs at 22° C. Then to block any unreacted —SH groups, N-ethylmaleimide was added to give a final concentration of 20 mM.

The pH of the vesicle-IL-2 suspension was then adjusted to pH 9. A CM-Sepharose column (50 mM Tris, pH 9.0) was drained. The liposomes were applied to the column, the resin stirred, incubated 10 min, and again drained to separate uncoupled interleukin-2 in control and test samples. Aliquots (0.5 ml) of buffer were added and fractions collected. All turbid or opalescent fractions were pooled and assayed.

As seen in FIG. 7, SATA-PE/SUVs that were deacetylated did compete in a receptor binding assay, when coupled to interleukin-2. However, no covalent attachment of interleukin-2 occurred using non-deacetylated SUVs, and removal of the uncoupled interleukin-2 yielded liposomes without interleukin-2 on the surface.

The procedure for coupling interleukin-2 to SUVs set forth in this Example has yielded liposomes having 6 to 5040 molecules of binding-domain protected interleukin-2 per 50 nm SUV.

To summarize the data in this Example, interleukin-2 is modified by first protecting the interleukin-2 receptor binding domain. After desorbing the modified interleukin-2 from the resin, the molecule is then covalently coupled to SUVs after exposing the sulfhydryl on the modified lipid which is acetylated until use. This reaction scheme utilizes both a stable liposome preparation and a bioactive form of interleukin-2. The use of antibodies, and in particular the use of antibodies bound to a stationary phase as described in this Example, may also be employed in conjunction with the interleukin-2 modification protocols described below in Examples 2–5.

EXAMPLE 2

Synthesis of an Extended Linker Arm to Alleviate Steric Hindrance

Figure 8:
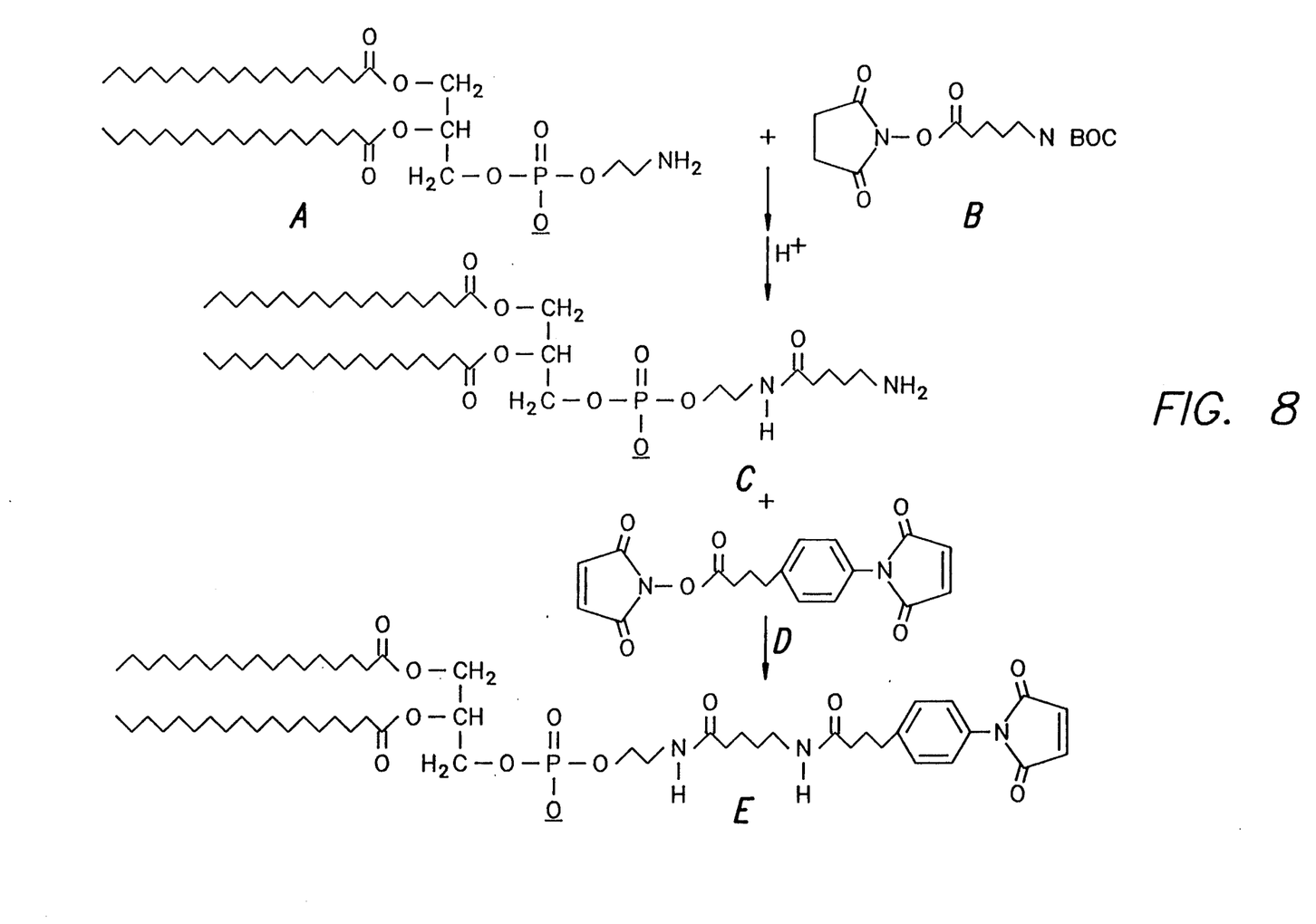

A preferred route to the synthesis (FIG. 8) of generally useful activated lipids is as follows. To a solution of distearoyl phosphatidylethanolamine (A) and succinimidyl-gamma-BOC-aminopentanoate (B) in chloroform-methanol, 9:1, is added a slight excess of triethylamine. The solvent is evaporated and the BOC group removed with a solution of trifluoroacetic acid in dichloromethane. The reaction of SMPB (D) with the distearoyl phosphatidylethyl-gamma-amino-pentanamide (C), left as residue after the trifluoroacetic acid reaction, is performed using the same conditions for the first coupling reaction. The distearoyl phosphatidylethyl-4-(p-maleimidophenyl- butyramide) pentanamide (E) is purified using silica gel chromatography.

After purification, the activated lipid is incorporated into liposomes whereby drug or marker is entrapped in the standard fashion. The liposomes are then ready for reaction with free protein sulfhydryls either present on the unmodified protein, or with derivatives prepared as described below.

For example, SATA may be used in limiting concentration. Thus, to a solution of interleukin-2 at about pH 8 may be added a solution of SATA in DMF or dioxane. The amount of substitution may be controlled by limiting the quantity of reagent. The sulfhydryl is then deblocked by the addition of hydroxylamine and the interleukin-2 protein immediately coupled to liposomes having the maleimido group on the surface.

EXAMPLE 3

Modification at Select (Limited) Lysine Sites on the Protein

The most abundant and available protein reaction sites are lysine amino groups. Since several of these appear to be involved in interleukin-2 receptor binding, any attempt to use the lysines as the residue for coupling must limit the lysines which actually undergo a reaction.

Figure 9:
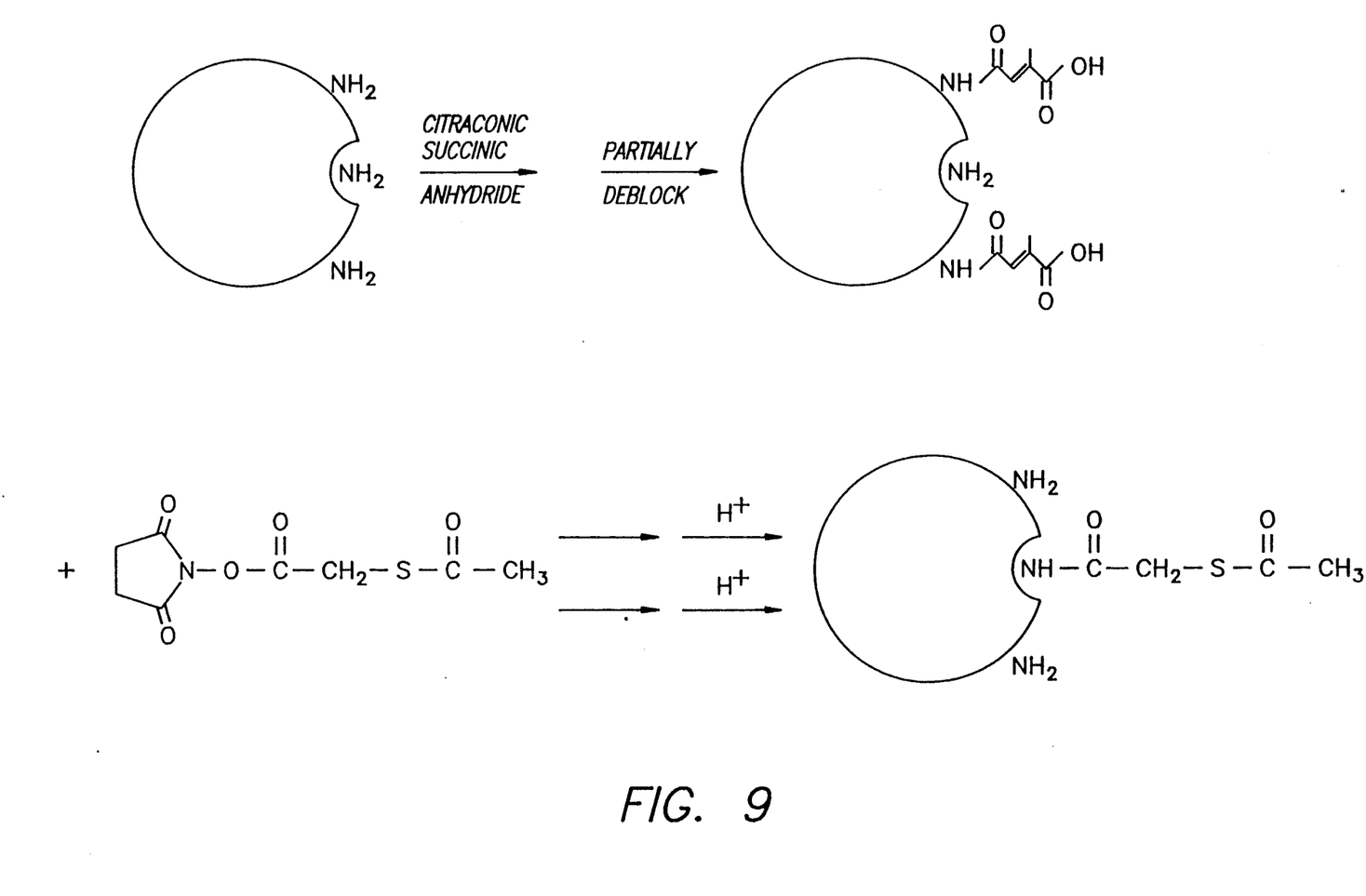
FIG. 9 depicts an alternate reaction for preparing derivatized interleukin-2 or other ligands and described in Example 3.

If the reactivity of the critical lysines is much faster or comparable to most of the other lysines, a second strategy may be employed. In this strategy, as shown in FIG. 9, essentially all but a few lysines are derivatized first with a reversible blocking agent. Using only enough reagent so that the most reactive or accessible lysines are blocked, or after blocking followed by partial deblocking, one then derivatizes the remaining lysines by using large excesses of a reagent which forms sulfhydryls. To a solution of interleukin-2 in borate buffer at pH 8.8 is added citraconic anhydride, maintaining the pH by addition of 1N sodium hydroxide. The citraconic acid groups can be removed at pH 2, and this reaction interrupted by again raising the pH. Excess SATA is added to the solution at pH 8.8, derivatizing all free amines. The excess reagent is removed by dialysis and the remaining citraconic acid groups removed at pH 2. The solution is brought to neutral pH and the sulfhydryl formed by addition of hydroxylamine. Liposomes, having the SMPB maleimido group, are introduced and coupled to the protein.

EXAMPLE 4

Modification at Arginine Sites on the Ligand

Figure 10:
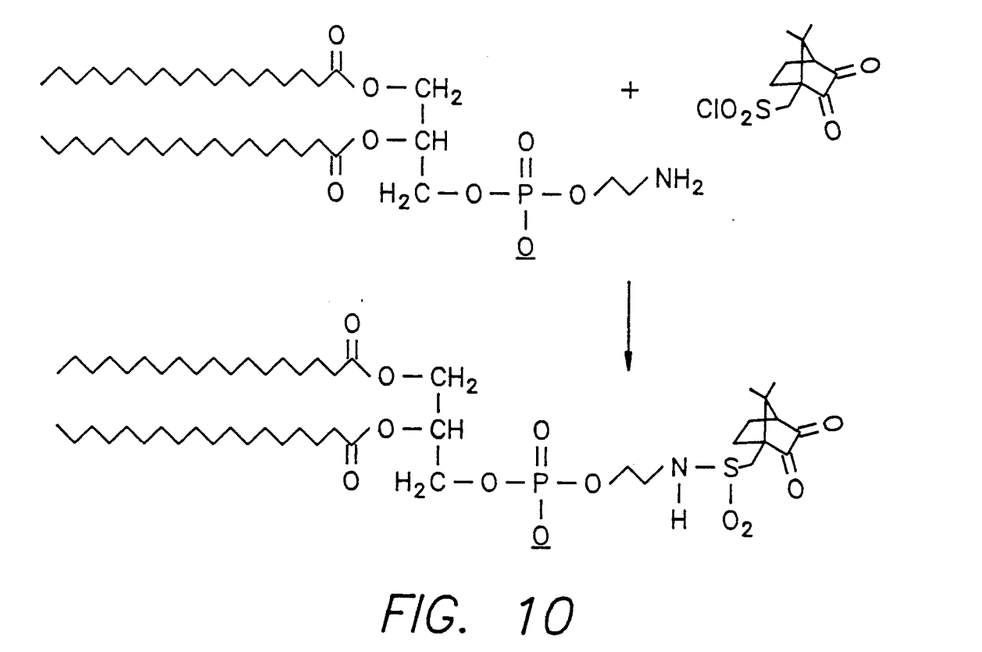
FIG. 10 depicts a reaction for the derivatization of arginine residues on interleukin-2 or other ligands.

There are four arginines in interleukin-2, only one of which appears to be in a region that might affect binding. Thus, liposomes may be linked to interleukin-2 using an arginine specific reagent such as camphoquinone-10-sulfonic acid, as shown in FIG. 10.

The camphorsulfonyl chloride, prepared using thionyl chloride, is added to PE in the presence of pyridine. The camphorsulfonyl PE is then incorporated into liposomes and, in borate buffer at pH 8.8, is reacted with interleukin-2. Vesicle-linked interleukin-2 is separated from unreacted protein on a Sephadex G-150 column or the equivalent.

EXAMPLE 5

Modification at Histidine Sites on the Ligand

Histidine may be chemically modified via reagents such as bromoacetamide compounds. His-70 of interleukin-2, in particular, does not affect binding activity. A heterobifunctional reagent based on bromoacetamide may be synthesized to give an attachment point for the liposome. Specifically, this is:

$$Br-CH_2-\overset{O}{\underset{\|}{C}}-NH-CH_2-CH_2-NH-\overset{O}{\underset{\|}{C}}-CH_2-S-\overset{O}{\underset{\|}{C}}-CH_3$$

This compound is prepared by addition of bromoacetylbromide to ethylene diamine (1:1) followed by reaction of the remaining amine with SATA. Reaction with interleukin-2 histidine in 1M acetate buffer pH 5.5 produces, at the histidine imidazole group, the 3'-N-substituted SATA derivative. Addition of hydroxylamine deacetylates the SATA label to give a free sulfhydryl group available for reaction with SMPB maleimido coupled liposomes.

EXAMPLE 6

Assays for Monitoring Receptor Binding Activity of the Liposome/IL-2

Anti-proliferation measurements were performed by growing cells possessing the high affinity interleukin-2 receptor for several days in:
 a. culture media in the absence of any form of interleukin-2,
 b. culture media supplemented with an effective dose of free cytostatic agent,
 c. culture media supplemented with a dose of the liposome/IL-2 complex of Example 1, and
 d. culture media supplemented with a dose of liposome/IL-2 complex of Example 1 containing a cytostatic agent.

After an appropriate treatment period determined in previous studies, the cells are pulse-labeled with $^3$H-thymidine. Following a 3–4 hour labeling period, all cultures are then harvested on glass-fiber filter strips and $^3$H-thymidine incorporation measured as an index of cellular proliferation. The effectiveness of the liposome/IL-2 containing cytostatic agent complex is thus determined by comparison to cells cultured in the absence of any form of the drug. In vivo biodistribution of the liposome/IL-2 complexes may be ascertained using known techniques, which are described in Example 7.

EXAMPLE 7

Biodistribution Studies

A preferred procedure for measuring biodistribution employs the radionuclide Indium-111. The liposome-encapsulated Indium will be in the form of one or two chelate complexes. For biodistribution studies measuring the in vivo fate of the liposome/IL-2 formulations, the chelator ethylenediamine tetraacetic acid (EDTA) is preferably used; for total in vivo uptake by target cells nitrilotriacetic acid (NTA) is preferably used.

In a conventional biodistribution study, SUVs of a given composition are prepared in the presence of chelator and Indium-111 for passive encapsulation of indium, or the ionophore A23187 for subsequent active encapsulation of Indium-111 into preformed liposomes. In either situation the liposomes are separated from unencapsulated materials by treatment with additional EDTA, followed by column chromatography.

Biodistribution measurements are conducted by injecting the study animals intravenously with the $^{111}$In-liposome/IL-2 complex. At several times after injection (for example at 1, 3, 6, and 24 hours), animals are sacrificed and tissues collected for gamma counting. Liposomes loaded with $^{111}$In-EDTA may be used for initial biodistribution studies. This tightly bound chelate complex allows measurement of in vivo retention times for the liposomes. Experiments performed relating to the present invention have shown that $^{111}$In-EDTA alone is rapidly cleared in vivo. Therefore, any recovered Indium-111 activity may be interpreted as $^{111}$In-liposome/IL-2.

Uptake of liposome/IL-2 by lymphocytes in a test animal may be studied using the $^{111}$In-NTA complex. This relatively weak chelate complex has been shown to maintain Indium-111 in the aqueous compartment of liposomes, but quickly to release Indium-111 once the chelate is in the proximity of protein or carbohydrate macromolecules. Therefore, treatment of study animals with $^{111}$In-NTA-liposome/IL-2 formulations provides a means for measuring cumulative uptake by lymphocytes.

This may be accomplished by treating animals with the $^{111}$In-NTA formulations. Test animals may be given single or multiple (2–3) injections of the $^{111}$In-NTA liposomes by either intravenous or intraperitoneal routes of administration. At various times after treatment, animals are sacrificed and lymphocytes isolated from, for example, blood, spleen, and peritoneum by centrifugation on Ficoll gradients. The isolated lymphocytes are then counted for indium-111 in a gamma counter. Biodistribution studies in healthy rats have shown that the $^{111}$In labelled $^{111}$In-liposome/IL-2 complex of Example 1 had extended circulation half life, and did not attach to macrophages or unactivated T cells.

In vivo biodistribution studies, in addition to directly measuring liposome interaction with T lymphocytes, may be used to evaluate the extent of uptake of the liposome/IL-2 formulations by the RES, particularly at liver, spleen and lymph node sites. It is widely known that many types of phospholipid vesicles are rapidly taken up in the liver and spleen, thus removing them from blood. Large liposomes and vesicles with various carbohydrate and protein groups attached are two particularly susceptible types. Therefore, the nature of the RES uptake is of importance to the practice of the present invention. Suitable doses may be established from such a test using standard procedures.

In order to avoid RES uptake of a non-specific nature and involving primarily macrophage, to the extent this presents a hindrance to liposome/lymphocyte interaction for a given liposome/interleukin-2 formulation, RES blockage by prior treatment with liposomes directed to RES sites may be employed. Alternatively, additional modification to the surface of liposome/interleukin-2 formulations, using for example a process similar to opsonization to enhance liposome interaction with blood lymphocytes by prolonging circulation times may be employed. Still further, RES uptake can be minimized by local administration of the interleukin-2 liposome preparation as a depot at the critical site, such as the site of a graft or an organ that is undergoing autoimmune attack.

The compounds cyclosporin A, mitomycin C, Ara C, daunorubicin, doxorubicin, cis-platinum, 6-mercaptopurine, actinomycin D, fluorodeoxyuridine, AZT, mephalan and methotrexate are examples of appropriate active agents for use in the present invention. For any such agents, separate studies may be performed to determine the encapsulation and subsequent release characteristics of the agent with the liposome formulation being tested. The range of drug administered is governed by the quantity given (volume) and the concentration (mgs/ml). Methotrexate is representative of a non-lipid soluble drug, and has been successfully encapsulated in amounts of 20 to 200 μg/mg lipid, which produces 0.3 mM methotrexate in aqueous liposome dispersion for administration. Methotrexate is passively encapsulated by sonicating the drug together with the described phospholipids in an aqueous buffer according to methods known in the art.

With respect to cyclosporin, as for example the Sandoz Sandimmune® product, intravenous administration of the pharmaceutical compound in treatment of organ transplantation of graft-versus-host disease is normally at a dosage of 3–5 mg/kg/day. Oral doses are higher by approximately a factor of three. When adminity of the pressure field of the medium external to the exhaust means 62 may require consideration. As is well known, in aircraft applications a position 180° from top dead center is a region of stable pressure. Therefore, for aircraft application it is suggested that the circumferential location of the exhaust means 62 be 180° from top dead center.

Referring now to FIGS. 2-4, the exhaust means 62 is located circumferentially adjacent to and upstream of, relative to the flow within the shell cavity 52, the nozzle 58. This location removes fluid which has transferred heat as it travelled around the circumference of the shell cavity 52. In effect, the exhaust means 62 removes relatively cool exhaust fluid from the shell cavity 52.

Figure 5:
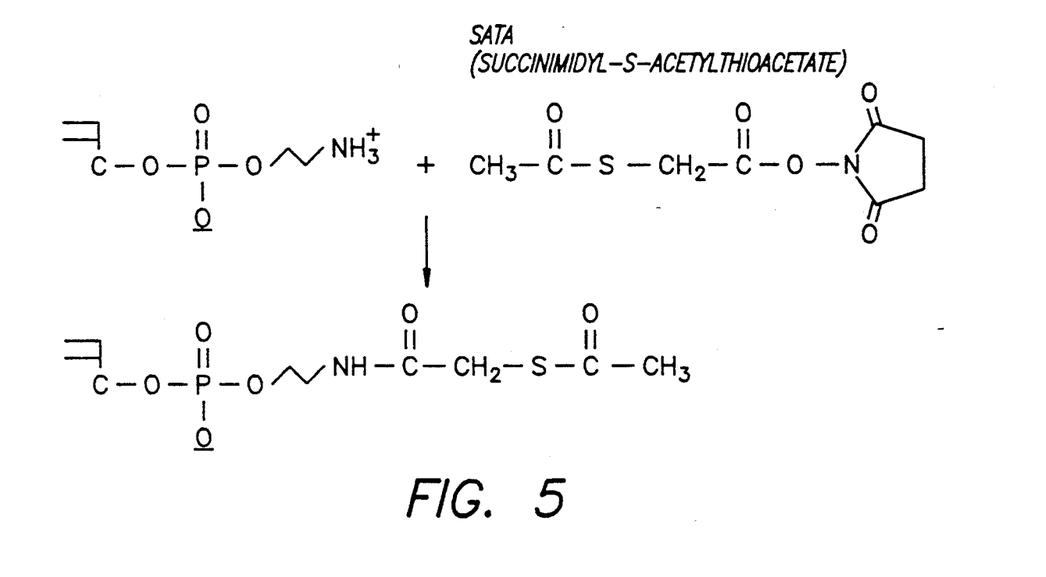

The exhaust means 62 includes a plurality of vanes 66, a plurality of exhaust slots 68, an upstream fairing 69, a downstream fairing 70, and an axially adjacent wall 72. The plurality of exhaust vanes 66 extend radially inward from the inlet shell 42 and into the shell cavity 52. The plurality of vanes 66 also extend axially. Each vane 66 is aerodynamically shaped to engage the body of fluid flowing circumferentially within the shell cavity. As shown in FIG. 5, the vanes have a rounded leading edge 74 which adapts the vanes to engage with fluid flowing at off angles relative to the circumferential direction. The roundness of the vane leading edge 74 is defined by the ratio of leading edge 74 diameter d, measured as shown in FIG. 5, to maximum thickness t, measured in the circumferential direction. To accommodate off angle flow within the shell cavity 52, it is suggested that the ratio d/t be between 0.4 and 0.6. The shape of the vanes 66 is also dependent upon the ratio of maximum thickness t to vane length l. It is suggested that the ratio t/l be between 0.3 and 0.5. While the vanes 66 have been described with respect to various ratios of length l, thickness t, and leading edge diameter d, it will be appreciated by those skilled in the art that the values of these ratios vary with application and the suggested ranges of values may be transgressed without departing from the scope of the invention.

Each of the exhaust vanes 66 is circumferentially adjacent to and downstream of, relative to the direction of flow of the body of fluid within the shell cavity 52, one of the plurality of exhaust slots 68. The plurality of exhaust slots 68 extend radially through the inlet shell 42 and provide means of communication between the shell cavity 52 and the external medium. The exhaust slots 68 are circumferentially adjacent and extend in an axial direction as shown in FIG. 4.

The upstream fairing 69 provides a smooth transition from the flow surface of the inlet shell 42 to the vanes 66. The downstream fairing 70 provides a smooth transition from the vanes 66 back to the flow surface of the inlet shell 42. The fairings 69, 70 eliminate abrupt changes in cross-sectional area within the shell cavity 52. In accordance with conventional fluid mechanics, the fairings 69, 70 produce smooth flow lines over the exhaust means 62 and uniformly distribute the exhaust flow through the exhaust slots 68. Without the fairings 69, 70, an unequal distribution of the flow through the slots would occur. Unequal distribution implies a flow separation, with corresponding flow losses and inefficiencies, within the shell cavity 52.

FIGS. 1-4 show exhaust means having five (5) vanes and six (6) slots. The quantity and size of the vanes and slots is dependent upon the flow characteristics of the shell cavity and the flow rate of the source of high temperature, high pressure fluid. The quantity and size of the vanes and slots must be sufficient to prevent over pressurization of the shell cavity when subjected to the maximum output of the source of hot fluid. In addition, the quantity and size of the vanes and slots must permit sufficient pressurization of the shell cavity to produce adequate flow velocity through the slots and penetration of the external flow. Temperature considerations dictate having multiple small slots to increase the rate of temperature decay of the fluid exiting each slot. A plurality of small slots produce a higher rate of temperature decay than a single large opening.

During operation of the gas turbine engine 16, compressor discharge fluid is removed from the diffuser case 25. The combustion section 26 is a source of high pressure, high temperature fluid (relative to the external medium) which may be used as heating fluid in the anti-ice system. The fluid is then flowed through the conduit 56, is ejected through the nozzle 58 and into the shell cavity 52. The conduit 56 provides means to flow the high temperature, high pressure fluid into the shell cavity 52. As shown in FIGS. 1 and 2, the fluid is ejected from the nozzle 58 in a direction tangential to the circumferential direction. The nozzle 58 provides means to inject fluid into the shell cavity 52 to generate a flowing body of fluid. The high pressure fluid exits the nozzle 58 with sufficient velocity to entrain the body of fluid within the shell cavity 52 and produce a body of fluid having a principal component of velocity directed in the circumferential direction.

Exhaust means 62 is necessary to prevent over-pressurization of the shell cavity 52. The exhaust means 62 removes fluid from the radially outermost and axially downstream section of the shell cavity 52. The exhaust vanes 66 turn a portion of the flow such that the exhaust fluid is ejected from the cavity with an ejection angle $\alpha$ defined by an the angle formed by the direction of the exhaust flow and the external surface of the nacelle, equal to 90°. Redirecting the flow to a direction substantially normal to the direction of flow of the external medium maximizes the rate of decay of temperature downstream of the exhaust slots 68.

The exhaust vanes 66 utilize the dynamic pressure head within the shell cavity in addition to the static pressure head to urge the fluid through the exhaust slots 68. The combination of dynamic and static pressure head produce an exhaust flow velocity sufficient to permit the exhaust flow to penetrate the external medium flowing by the exhaust slots 68. By penetrating the external medium a separation is created between the hot exhaust fluid and the nacelle 18. The separation region is a low pressure region which pulls in low temperature external medium. As a result, the exhaust fluid mixes with external medium rather than reattaching to the surface of the nacelle 18. In addition, the high velocity of the exhaust flow permits the total area of the exhaust slots 68 to be reduced relative to prior art exhaust vents.

Figure 6:
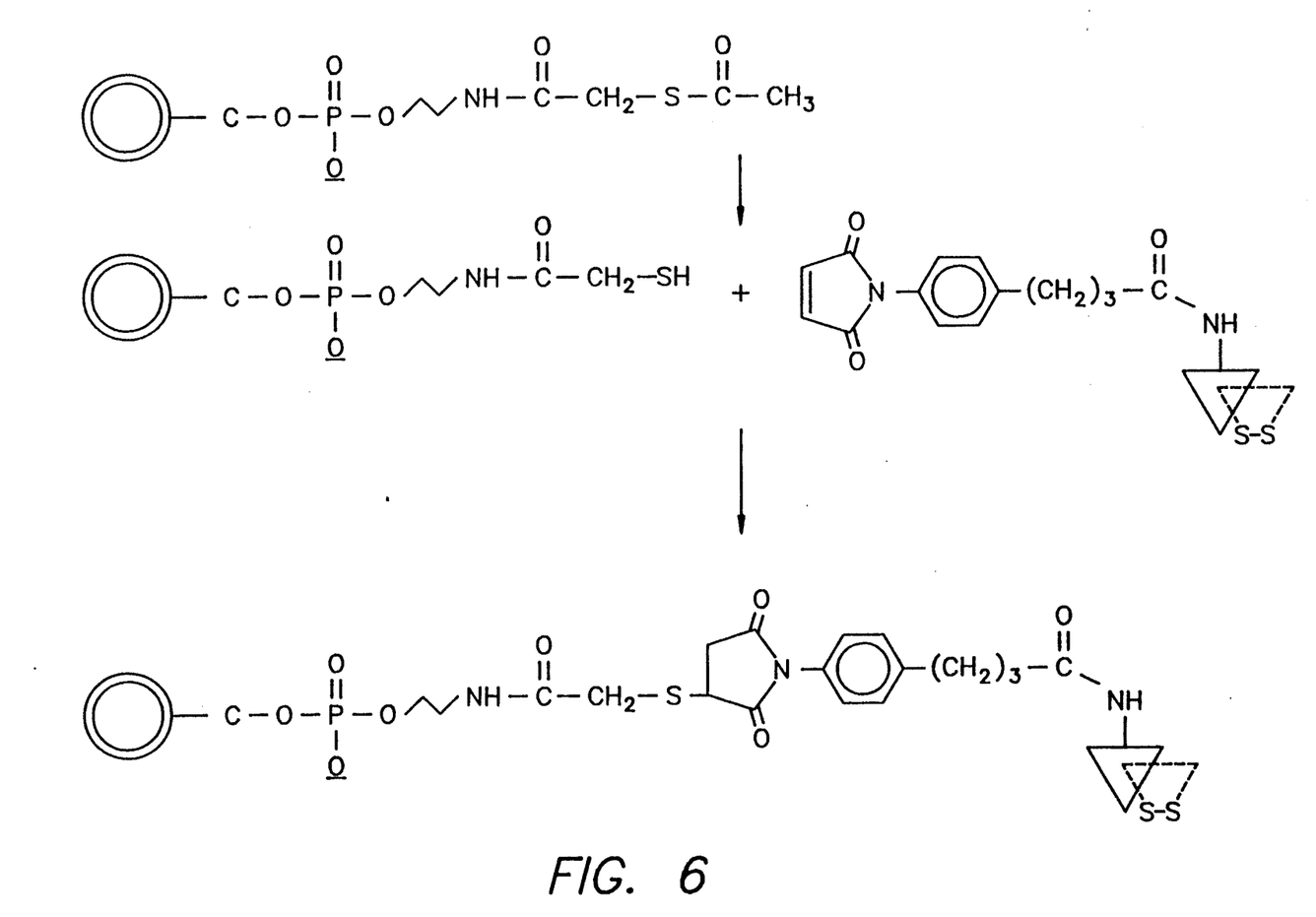
Figure 7:
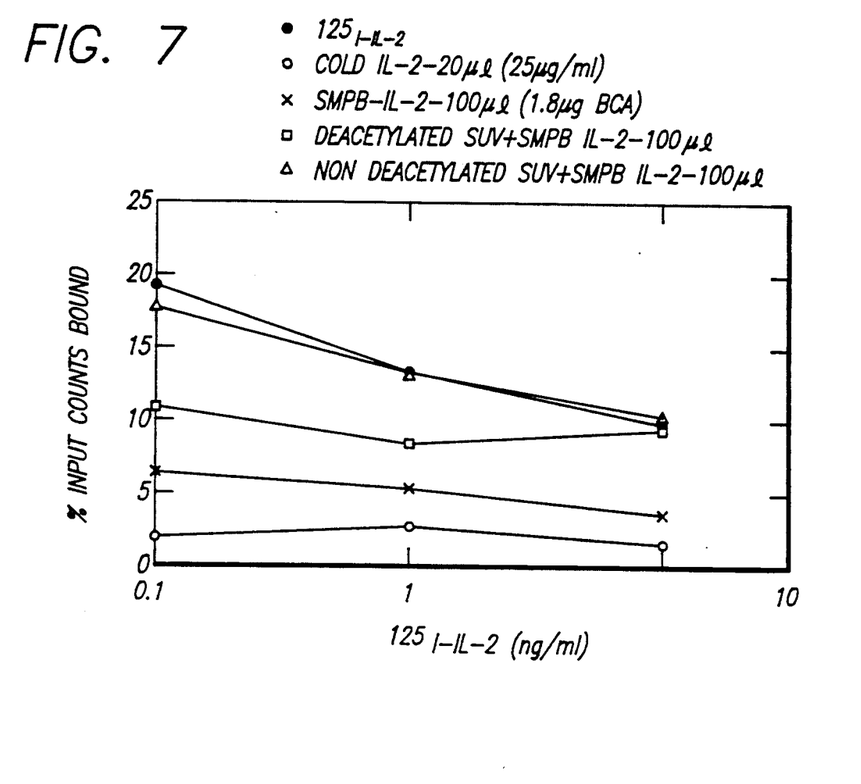

FIG. 6 is an illustration of test results of measured temperature decay as a function of distance downstream. Temperature decay is the ratio of the difference between surface temperature T and free stream temperature $T_\infty$ to the difference between vent exit temperature $T_0$ and free stream temperature $T_\infty$. Distance downstream is shown as a ratio of x/D, where x is the actual distance and D is the effective diameter of the vent. Effective diameter D is the diameter of a circle equal in area to the vent. In this way the downstream distance is non-dimensional and the size of the vent is parametrically accounted for. The vanes provide means istered using the delivery vehicles of the present invention, lower dosages may be expected to achieve comparable active effects in view of the targeted delivery of the drug to immune system cells responsible for the disease conditions.

Activated T Cell Specificity

Efficacy of liposome/IL-2 preparations may be demonstrated using animal models in which T lymphocytes can be reproducibly activated. Two models that are readily available are the rat skin allograft model and rat burn model (30% body surface). Using either model, groups of animals would receive either liposome/IL-2 containing the immunosuppressive drug, or only liposome/IL-2. Retention of the allograft as the animal undergoes a protocol of liposome/IL-2 treatment is then measured. Those receiving liposome/IL-2 without the liposome-incorporated drug will readily reject the graft due to presence and cytolytic activity of activated T cells in the area of the graft. Alternatively, liposome-/IL-2 containing a drug of choice may also be used in the course of either the rat or mouse leukemia models. Tests have shown that the liposome/IL-2 conjugate of Example 1 is attracted to activated T cells in vitro.

The present delivery vehicles may be used in a variety of therapeutic contexts, including mammalian disease therapy and in vivo diagnosis, and biodistribution studies have shown significant advantages. When practiced using small unilamellar liposomal liposomes, which have been shown both to be useful in targeting solid tumors and to have greater circulation times than other vehicles, the present delivery vehicles may be used to deliver medicinal agents or diagnostic markers (as for example radioactive labels, fluorescent molecules and NMR-imaging agents such as magnetite) to neoplastic cells or particular organs of the body such as the liver. As contemplated herein, where the cell population of interest is characterized by a cellular receptor such as the interleukin-2 receptor, the present delivery vehicles may be utilized to deliver cytotoxic, regulatory, diagnostic or other molecules in a targeted manner. Thus, in the case of the liposome/IL-2 delivery vehicle of the present invention, active agents may be delivered to lymphocytes so as to treat, regulate or diagnose conditions involving malfunction of the immune system (including genetic or non-genetic autoimmune diseases such as rheumatoid arthritis, juvenile onset diabetes, systemic lupus erythematosus and others, as well as transplantation responses such as graft-versus-host disease), lymphocyte-related cancers (including lymphomas and leukemias such as adult or chronic myelogenous leukemias and hairy-cell leukemia) and T helper cell disorders (including viral disorders such as those associated with HIV-infected T cells).

The foregoing description is intended to present the preferred embodiments that may be utilized in practicing the present invention, but it will be apparent to those skilled in the art that modifications and equivalents may be incorporated without departing from the scope and spirit of the invention. It is therefore intended that the invention be limited only by the terms of the following claims.

We claim:

1. A process for preparing a liposome/cytokine complex, comprising coupling a liposome to a cytokine having a receptor binding domain capable of interacting with a cell receptor site with the receptor binding domain on the cytokine having been protected by an antibody prior to the coupling, the coupling occurring at a lysine residue of the cytokine which is not within the receptor binding domain.

2. The process of claim 1 in which the cytokine is an interleukin-2.

3. The process of claim 1 or 2 in which the coupling includes the steps of:
  a) covalently binding the liposome to a first coupling agent comprising a sulfo-n-hydroxy succinimidyl compound;
  b) binding the cytokine to a second coupling agent comprising a member of the group consisting of:
  succinimidyl-4-(p-maleimidophenyl) butyrate,
  sulfo-succinimidyl-4-(p-maleimidophenyl) butyrate,
  N-(4-carboxy-cyclohexyl-methyl) maleimide,
  sulfo-N-(4-carboxy-cyclohexyl-methyl) maleimide,
  m-maleimidobenzoyl-N-hydroxysuccinimide ester,
  sulfo-m-maleimidobenzoyl-N-hydroxysuccinimide ester,
  N-succinimidyl (4-iodoacetyl) aminobenzoate,
  sulfo-N-succinimidyl (4-iodoacetyl) aminobenzoate; and
  c) joining the first and second coupling agents to anchor the cytokine to the liposome, leaving the receptor binding site of the cytokine physically available for interaction in vivo.

4. The process of claim 3 in which the first coupling agent is succinimidyl-S-acetylthioacetate and the second coupling agent is succinimidyl-4-(p-maleimidophenyl) butyrate.

* * * * *